United States Patent
Wang et al.

(10) Patent No.: US 10,238,298 B2
(45) Date of Patent: Mar. 26, 2019

(54) METHOD AND APPARATUS FOR PHOTOACOUSTIC TOMOGRAPHY USING OPTICAL ORBITAL ANGULAR MOMENTUM (OAM)

(71) Applicant: NEC Laboratories America, Inc., Princeton, NJ (US)

(72) Inventors: Ting Wang, West Windsor, NJ (US); Yi Weng, Lafayette, LA (US)

(73) Assignee: NEC Corporation (JP)

( * ) Notice: Subject to any disclaimer, the term of this patent is extended or adjusted under 35 U.S.C. 154(b) by 670 days.

(21) Appl. No.: 14/979,034

(22) Filed: Dec. 22, 2015

(65) Prior Publication Data
US 2016/0198954 A1 Jul. 14, 2016

Related U.S. Application Data

(60) Provisional application No. 62/101,078, filed on Jan. 8, 2015.

(51) Int. Cl.
*A61B 5/05* (2006.01)
*A61B 5/00* (2006.01)

(52) U.S. Cl.
CPC .......... *A61B 5/0095* (2013.01); *A61B 5/7285* (2013.01); *A61B 2576/00* (2013.01)

(58) Field of Classification Search
None
See application file for complete search history.

(56) References Cited

U.S. PATENT DOCUMENTS

| 8,614,707 | B2 | 12/2013 | Warsito et al. | |
|---|---|---|---|---|
| 2009/0324248 | A1 | 12/2009 | Shiraki | |
| 2012/0078082 | A1 | 3/2012 | Elgort et al. | |
| 2012/0207470 | A1* | 8/2012 | Djordjevic | H04B 10/25 398/44 |
| 2013/0173194 | A1* | 7/2013 | Dholakia | G02B 27/58 702/71 |
| 2015/0260650 | A1* | 9/2015 | Ashrafi | G01N 21/17 702/25 |

FOREIGN PATENT DOCUMENTS

CN 103292900 A 9/2013

OTHER PUBLICATIONS

Yamane et al (frequency-resolved measurement of the orbital angular momentum spectrum of fentosecond ultrabroad optical-vortex pulses based on field reconstruction).*
Treeby et al (photoacoustic tomography in absorbing acoustic media using time reversal).*
Askar et al (Numerical computations pf radial vibrations of axially polarized piezoelectric circular cylinder).*

(Continued)

*Primary Examiner* — Joel F Brutus
(74) *Attorney, Agent, or Firm* — Joseph Kolodka

(57) ABSTRACT

A method and system for remote sensing. The method includes applying an orbital angular momentum (OAM) mode on a light beam to generate an OAM light beam having an optical OAM spectrum, exposing a target object to the OAM light beam such that the target object absorbs energy of the OAM light beam to generate ultrasonic emissions, the ultrasonic emissions having a reflected OAM spectrum associated with the target object, and generating a high resolution image of the target object based on the reflected OAM spectrum.

20 Claims, 6 Drawing Sheets

(56) References Cited

OTHER PUBLICATIONS

Balas, C., "Review of biomedical optical imaging—a powerful, non-invasive, non-ionizing technology for improving in vivo diagnosis," Measurement Science and Technology, vol. 20, No. 10, Sep. 2009. (pp. 1-13).

Boppart, S.A. et al., "Point-of-care and point-of-procedure optical imaging technologies for primary care and global health," Science Translational Medicine, vol. 6, No. 253, Sep. 2014. (pp. 1-25).

Cvijetic, N. et al., "Detecting Lateral Motion using Light's Orbital Angular Momentum," Scientific Reports, Oct. 2015. (pp. 1-7).

Dong, C. et al., "Accelerated Nonlinear Multichannel Ultrasonic Tomographic Imaging Using Target Sparseness," IEEE Transactions on Image Processing, vol. 23, No. 3, Mar. 2014. (pp. 1379-1393).

Lavery, M.P.J., et al., "Refractive elements for the measurement of the orbital angular momentum of a single photon," Optics Express vol. 20, No. 3, Jan. 2012. (pp. 1-6).

Lutzweiler, C. et al., "Optoacoustic Imaging and Tomography: Reconstruction Approaches and Outstanding Challenges in Image Performance and Quantification," Sensors, vol. 13, No. 6, Jun. 2013. (pp. 7345-7383).

Salehi H.S. et al., "Design of miniaturized illumination for transvaginal co-registered photoacoustic and ultrasound imaging," Biomedical Optics Express vol. 5, No. 9, Aug. 2014. (pp. 1-6).

Wang, L. et al., "Photoacoustic Tomography: In Vivo Imaging from Organelles to Organs," Science, vol. 335, Mar. 2012. (pp. 1458-1462).

Weng, Y. et al., "Biomedical Photoacoustic Imaging Sensor based on Orbital Angular Momentum Multiplexing," Photonics North, Jun. 2015. (1 Page).

Winzer, P.J., "Making spatial multiplexing a reality," Nature Photonics, vol. 8, May 2014. (pp. 345-348).

Yao, A.M. et al., "Orbital angular momentum: origins, behavior and applications," Advances in Optics and Photonics, vol. 3, No. 2, May 2011. (pp. 161-204).

\* cited by examiner

METHOD AND APPARATUS FOR PHOTOACOUSTIC TOMOGRAPHY USING OPTICAL ORBITAL ANGULAR MOMENTUM (OAM)

RELATED APPLICATION INFORMATION

This application claims priority to provisional application Ser. No. 62/101,078 filed on Jan. 8, 2015, incorporated herein by reference.

BACKGROUND

Technical Field

The present invention generally relates to methods and systems for photoacoustic tomography. More particularly, the present disclosure is related to photoacoustic tomography using orbital angular momentum (OAM).

Description of the Related Art

Biological and medical imaging technology has been implemented to spatially localize, diagnose, and treat human diseases in a clinical setting. However, most existing biomedical imaging technologies are anatomical, and do not have the capacity to molecularly interrogate a tissue, such as indicating whether a tissue is cancerous or whether the tissue is responding to a particular therapy treatment.

Common imaging technologies include magnetic resonance imaging (MRI), x-ray computed tomography (CT), ultrasonography (US), single photon emission computed tomography (SPECT), and positron emission tomography (PET). These common imaging technologies, however, are still in the pre-clinical phase of experimentation based on the physical characteristics. For instance, MRI technology does not display functional information and has a very high cost, although it provides strong anatomical contrast between soft tissues. CT technology makes use of harmful ionizing radiation, which causes the frequency of use to be limited. In addition, the images produced by CT technology differentiate very little among varying soft tissues. Another imaging technology is ultrasound technology, however, traveling acoustic waves implemented by ultrasound technology are impeded by abrupt changes in density of, for example, bone and/or air, and contrast suffers greatly among soft tissues because the variations in density are relatively minor. Moreover, some imaging technologies, including OCT and US, are strongly affected by speckle interference, which is displayed as random intensity patterns produced by the interferences of a set of wavefronts (e.g., waves having the same frequency, but having different phases and amplitudes). As the reflecting surface is not perfect, an abundance of waves with different phases are generated.

Common optical imaging techniques include diffuse optical tomography (DOT), optical coherence tomography (OCT), angular domain imaging (ADI), fluorescence imaging, and near infrared spectroscopy (NIS). However, these imaging technologies and/or techniques suffer from poor spatial resolution, which is associated with the high scatter of photons in human tissue. Consequently, current biological and medical imaging technologies cannot provide high resolution features, such as absorption contrast, structural imaging, and/or molecular imaging in biological tissues.

SUMMARY

In one embodiment, a method for remote sensing using orbital angular momentum (OAM)-based photoacoustic tomography for object recognition is provided. In an embodiment, the method may include applying at least one orbital angular momentum (OAM) mode on a light beam to generate an OAM light beam having an optical OAM spectrum, exposing a target object to the OAM light beam such that the target object absorbs energy of the OAM light beam to generate ultrasonic emissions, the ultrasonic emissions having a reflected OAM spectrum associated with the target object, and generating a high resolution image of the target object based on the reflected OAM spectrum In another embodiment of the present principles, a receiver for remote sensing using orbital angular momentum (OAM)-based photoacoustic tomography for object recognition is provided. In an embodiment, the receiver may include at least one transducer configured to detect ultrasonic emissions generated by a target object, wherein the ultrasonic emissions include a reflected orbital angular momentum (OAM) spectrum associated with the target object, at least one OAM detector configured to detect the reflected OAM spectrum, and an image processing device having a processor to generate a high resolution image of the target object based on the reflected OAM spectrum.

In yet another embodiment, a system for remote sensing using orbital angular momentum (OAM)-based photoacoustic tomography for object recognition is provided. In an embodiment, the system may include a drive signal generating circuit to generate an imaging synchronization signal of a light beam, at least one orbital angular momentum (OAM) detector to detect a reflected OAM spectrum, wherein the reflected OAM spectrum is provided by ultrasonic emissions generated from a target object absorbing energy of an OAM light beam, and an imaging processing device having a processor configured to compare a frequency of the synchronization signal with a frequency of the reflected OAM spectrum to generate a high resolution image of a target object.

These and other features and advantages will become apparent from the following detailed description of illustrative embodiments thereof, which is to be read in connection with the accompanying drawings.

BRIEF DESCRIPTION OF DRAWINGS

The present principles will provide details in the following description of preferred embodiments with reference to the following figures wherein.

DETAILED DESCRIPTION OF PREFERRED EMBODIMENTS

Systems and methods for photoacoustic tomography using orbital angular momentum (OAM) are provided. Main challenges in biological imaging technologies include providing optical biomedical diagnostic and high resolution imaging, including strong anatomical contrast between soft tissues, using non-harmful ionizing radiation, and reducing speckle pattern effect due to variations in intensity patterns. The present principles disclosed herein provide OAM-based photoacoustic tomography to provide high-resolution imaging with improved spatial resolution and multiplexing capabilities, high penetration depth and selectivity, high scanning speeds, sensitive optical absorption contrast, low acoustic scattering, while employing non-ionizing radiation.

Photoacoustic tomography, which may include optoacoustic (OA) or thermo-acoustic (TA) effect, refers to the generation of acoustic waves from a remote object being illuminated by pulsed or modulated electromagnetic (EM) radiation. For example, photoacoustic tomography is a technique that reconstructs an internal photoacoustic source distribution from measurements acquired by scanning detectors over a surface of an object. In an embodiment of the present principles, photoacoustic tomography is applied to an object, where absorption of externally applied radiation of pulsed electromagnetic (EM) waves may provide a temperature increase, thereby resulting in thermal expansion inside the object. Accordingly, the present principles may be used in connection with the biomedical field because of the advantages of ultrasonic resolution in combination with EM absorption contrast.

In one embodiment, the methods, systems and computer program products disclosed herein employ OAM-based photoacoustic tomography to obtain high resolution feature identification of structural properties. Orbital angular momentum (OAM) of light is a component of angular momentum of a light beam, such as the amount of rotation present in the light beam, that is dependent on the field spatial distribution (e.g., wavefront shape), and not on the polarization (e.g., property of the wave which may oscillate in more than one orientation). When a beam of light is shone onto an object (e.g., a target object), the beam of light carries energy and momentum, and the beam may be rotating around its own axis while it propagates forward in a substantially straight line. This rotational movement is referred to as the angular momentum of light, which may be expressed as a vector quantity representative of the amount of rotation present in the electromagnetic field of the light.

It should be understood that embodiments described herein may be entirely hardware, or may include both hardware and software elements which includes, but is not limited to, firmware, resident software, microcode, etc.

Figure 1:
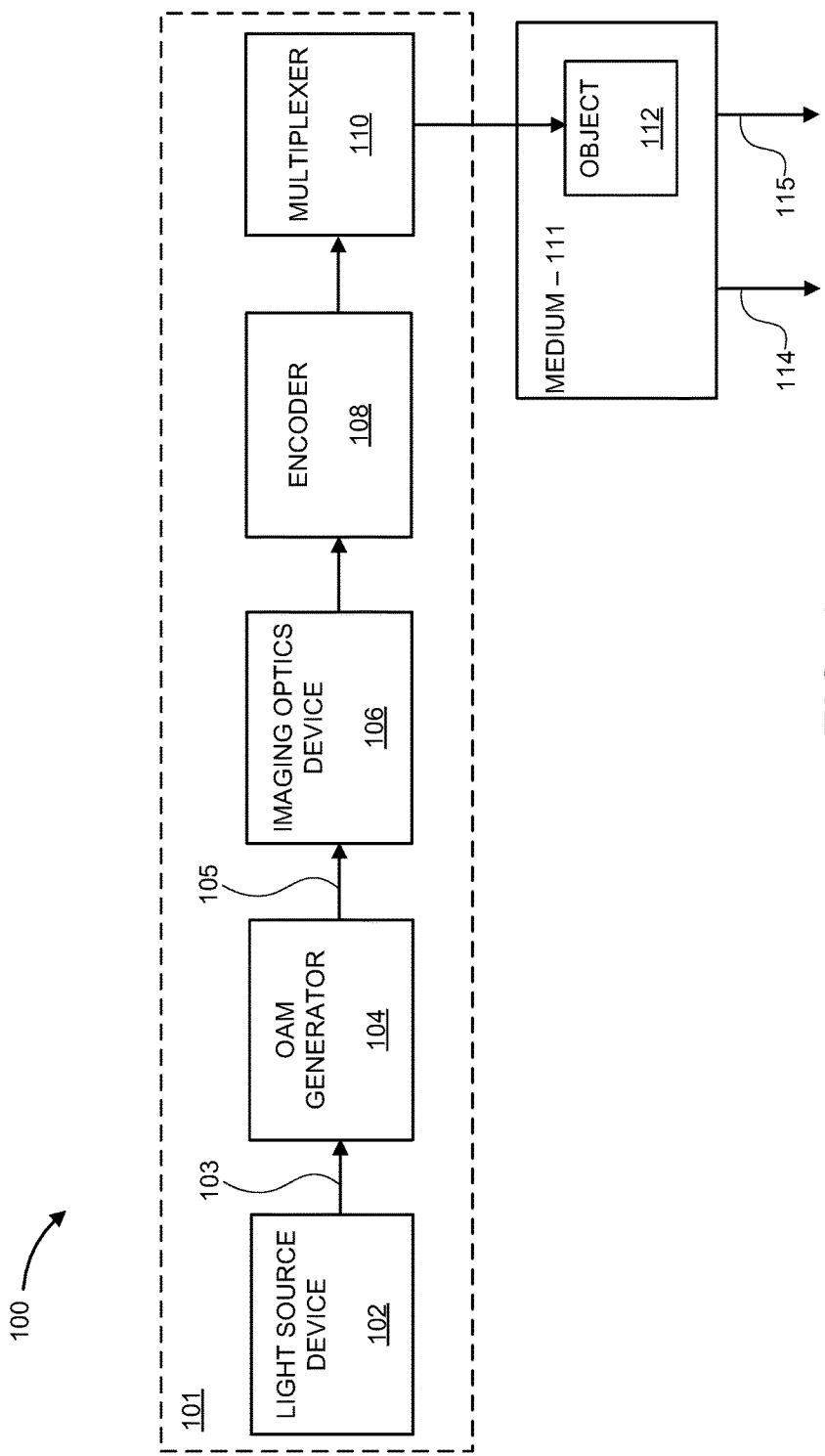
FIG. 1 shows an exemplary system for a transmitter-side remote sensing system using photoacoustic tomography with orbital angular momentum (OAM) for object recognition of a target object, in accordance with an embodiment of the present principles.

Referring to the drawings in which like numerals represent the same or similar elements and initially to FIG. 1, an optical OAM-based photoacoustic tomography method/system 100 for object recognition is illustratively depicted. In one embodiment, the optical OAM-based photoacoustic tomography method/system 100 may include a transmitter 101. The transmitter 101 may include a light source modulator for providing a light beam output for imaging a target object, such as at least one light source device 102. The light source device 102 may be configured to transmit a light beam 103 toward a target object 112. In some embodiments, the light source device 102 may include a laser beam source, such as a continuous wave (CW) laser, a pulsed laser, a time-variant laser beam, etc. For illustrative purposes, additional types of light source devices and/or laser beam sources may include, but are not limited to, vertical-cavity surface-emitting lasers (VCSELs), optical fiber laser, external cavity laser, solid state laser, high coherence light source, supercontinuum light source, quantum cascade laser, etc.

In an embodiment, a continuous wave laser (e.g., a frequency-swept laser source) may be employed to produce a continuous output beam, the continuous output beam having an electromagnetic wave of constant amplitude and/or frequency. In another embodiment, a pulsed laser (e.g., Q-switched lasers, mode-locked lasers, etc.) may be employed to provide a pulsed output beam such that the optical power is generated in pulses of some duration and/or at some repetition rate. For example, a pulsed laser may provide pulses of energy having very high energy values when the repetition rate is decreased, since pulse energy is equal to the average power divided by the repetition rate.

The light beam 103 may intrinsically have angular momentum. Generally, angular momentum is the rotational direction of linear momentum and/or a measurement of the quantity of rotation about a particular linear axis. In paraxial approximation, which is an approximation used in Gaussian optics and ray tracing of light through an optical system (e.g., a lens), the light beam's 103 angular momentum may be separated into two parts, namely spin angular momentum and orbital angular momentum (OAM). The spin angular momentum of light is associated with light's polarization degree of freedom, such as a wave's circular or elliptical polarization. For example, an electromagnetic wave may have circular polarization when its electric and magnetic fields rotate continuously around the axis of the light beam during propagation. In contrast, the orbital angular momentum (OAM) of light is associated with light's spatial degree of freedom.

According to an embodiment of the present principles, the transmitter 101 of the optical OAM-based photoacoustic tomography method/system 100 may include at least one optical OAM generator 104. The OAM generator 104 may configured to receive the light beam 103 from the light source device 102 and may generate at least one OAM mode on the light beam 103 to generate an OAM light beam 105 and/or an optical OAM spectrum directed towards the target object 112. In an embodiment, the OAM generator 104 may alter and/or modify one or more properties of a periodic waveform of the light beam 103 with a modulating signal that may include information to be transmitted via the OAM light beam 105.

In an embodiment, the OAM generator 104 may apply OAM modes on the light beam 103 to generate the OAM light beam 105 and/or an optical OAM spectrum directed towards the target object 112. A reflected acoustic OAM spectrum 114 may provide high resolution imaging information (e.g. a high resolution image) of the target object 112, as will be described in further detail below. An OAM light beam 105 carrying at least one OAM mode may be described in terms of Laguerre-Gaussian (LG) modes, which form a complete infinite-dimensional basis for the solutions of the paraxial wave equation. In an embodiment, the normalized LG mode at its beam waist may be expressed in cylindrical coordinates as:

$$LG_{m,p}(\rho, \varphi) = \left(\frac{2\,p!}{\pi(|m|+p)!}\right)^{1/2} \frac{1}{\eta}\left(\frac{\sqrt{2}\,\rho}{\eta}\right)^{|m|} L_p^{|m|}\left(\frac{2\rho^2}{\eta^2}\right) \exp\left(-\frac{\rho^2}{\eta^2}\right) \exp(im\varphi);$$

where m represents the on-axis phase singularity of strength, which may take any integer number and determines the azimuthal phase dependence of the mode. In the above equation, p represents an index that determines the radial shape or node number of the light distribution, which may take any non-negative value, $\rho$ is the radial cylindrical coordinate, $\varphi$ is the azimuthal angle, $\eta$ is the beam waist, and $L_p^{|m|}$ is the associated Laguerre polynomial.

In particular, light's spatial modes with complex amplitude described by the phase factor exp(il$\theta$) are known as its OAM modes, where l=0, ±1, ±2, . . . , and $\theta$ is the cylindrical coordinate. In one embodiment, the OAM generator 104 may apply arbitrary non-zero (l≠0) OAM states on the light beam 103 of the light source 102 to generate the OAM light beam 105, where l denotes the OAM phase number and/or OAM state number on the OAM light beam 105. An OAM light beam 105 carrying non-zero OAM states and/or modes may be defined as having a helical mode, which may be characterized by a wave front including a helix shape with an optical vortex in the center at the beam axis. When the OAM state is zero (e.g., l=0), for example, the light beam does not bear OAM, and accordingly is not helical and has a constant phase across the mode. According to the present principles, both the zero (e.g., l=0) and non-zero (e.g., l≠0) OAM modes and cases are supported.

In one embodiment, the optical OAM generator 104 may include a spatial light modulator (SLM), Q-phase plates, spiral phase plates, computer generated holograms, an OAM sorter, fiber-optic methods (e.g., generating an OAM mode in an optical fiber), integrated silicon photonics methods, etc. For example, a spatial light modulator (SLM) may include a device configured to impose spatially varying modulation on a beam of light, such as a modulation on the intensity and/or phase of a beam of light. In another example, Q-phase plates may include a liquid crystal cell having a thickness and/or birefringence selected to induce a birefringent phase at the wavelength for light propagation and may be employed to cause, for example, interaction between the spin angular momentum and orbital angular momentum. In yet a further example, the optical OAM generator 104 may include beta-barium borate (BBO) non-liner crystal. Barium borate may include non-liner optical material which may be transparent material.

In a further embodiment, the transmitter 101 may include at least one imaging optics device 106. In an alternate embodiment, the transmitter-side optical OAM-based photoacoustic tomography system 100 includes the at least one imaging optics device 106 such that the imaging optics device 106 is separate and apart from the transmitter 101. For ease of illustration, the at least one imaging optics device 106 is shown as a part of the transmitter 101. As shown in FIG. 1, following the OAM generator 104, the OAM light beam 105 may be applied as input to at least one imaging optics device 106, according to one embodiment.

The at least one imaging optics device 106 may include, but is not limited to, a lens, a plurality of lenses arranged in a series, microscope objective(s), or free-space optics, etc. In an embodiment, the at least one imaging optics device 106 may be configured to collimate the OAM light beam 105 to a fixed size, expand the light beam 105 to a larger size, reduce the size of the light beam 105 to a smaller size, or any combination thereof, image an object from a distance such that it is in focus to the detector, and/or image an object from an arbitrary distance such that it is in focus at the detector. In one embodiment, the at least one imaging optics device 106 may include a collimator. For example, a collimator may align the wavelengths of the OAM light beam 105 such that the wavelengths are parallel to each other. Collimating light beams include various advantages, including, but not limited to, minimizing the dispersion the wavelengths/light as the light beam propagates.

The transmitter 101 and/or the transmitter-side optical OAM-based photoacoustic tomography system 100 may include at least one encoder 108, as shown in FIG. 1. The encoder 108 may include any device configured to convert information from one format into another, such as a transducer and/or optical encoder. In one embodiment, the encoder 108 may be configured to convert the optical properties of the OAM light beam 105 into acoustic input. In further embodiments, the encoder 108 may determine position or orientation of the OAM light beam 105 for use as a reference or active feedback to control position. In an embodiment, the encoder 108 may encode the OAM light beam 105 at different positions in the wavelength domain of the OAM light beam 105.

For example, the OAM modes on the OAM light beam 105 may be encoded and/or decoded at certain wavelengths with high speed by electro-optic tuning of the OAM mode order of ring cavity. The encoder 108 may include a ring cavity, several download units each with an arc waveguide and a grating, and/or a bus waveguide. When the input OAM light beam 105 is injected from the input-port of bus of the encoder 108, the OAM light beam 105 may be coupled into the ring and propagate along the ring as whispering-gallery-mode (WGM) and downloaded by each of the arc waveguides, if the input OAM light beam 105 satisfies the resonance condition of the ring cavity. Otherwise, the OAM light beam 105 may pass through the thru-port of the bus waveguide. The download units may be equally coupled to the ring and equidistantly distributed around the circle so as to encode azimuthally dependent OAM modes, as the phase shift of propagating light at each downloaded unit may be successively varied. The OAM light beam 105 propagating in all arc waveguides may be combined and transformed into free space light at the end of gratings by the encoder 108. Examples of encoding devices may include, but are not limited to, Mach-Zehnder interferometers and/or gratings.

In a further embodiment, the transmitter 101 and/or the transmitter-side optical OAM-based photoacoustic tomography system 100 may include at least one multiplexer 110. In an embodiment, the multiplexer 110 may multiplex the OAM light beam 105 at different positions in the wavelength domain. For example, the multiplexer 110 may merge (e.g., multiplex) a number of signals of the OAM light beam 105 into a single signal or vice versa. In one embodiment, the multiplexer 110 may include a beam splitter which may split the OAM light beam 105 into two or more beams having the same and/or different optical properties. For example, a beam splitter may be configured to adjust the wavelength of the OAM light beam 105. In a further embodiment, a beam splitter may be configured to combine multiple beams into a single beam.

For example, during OAM multiplexing, the multiplexer 110 may convert the OAM light beam 105 from each L-dependent fiber-optic array into azimuthally dependent OAM modes. Examples of types of multiplexing devices that may be employed as the multiplexer 110 may include, but are not limited to, a photonic lantern, a near-field line-of-sight (LOS) multiplexer, etc. In some embodiments, the multiplexer 110 may be considered a complex coherent-detection based implementation with multiple input multiple output (MIMO) digital signal processing (DSP). In further embodiments, when the transmitter performs in a reflective mode, which is described in further detail below, the multiplexer 110 may include one or more OAM sorters and/or a single-mode fiber (SMF) optic array. For example, the multiplexer 110 may be configured to perform demultiplexing such that when input acoustic waves carrying the OAM modes is input into the OAM sorters, the twisting phase fronts of OAM modes may be converted into L-dependent spatial positions via a log polar optical element transformation at its output, whereas the multiplexer 110, such as a single mode optical fiber array, may collect acoustic waves from each L-dependent spot for coherent detection, and therefore operates as a demultiplexer.

In an embodiment, the OAM light beam 105 may be transmitted towards the target object 112 through a medium 111. The medium 111 may include, but is not limited to, glass, water, solution, air, and/or transparent container devices or similarly functioning components which surround the target object 112. For example, the OAM light beam 105 may be transmitted through a water tank, functioning as the medium 111, where the target object 112 is contained therein. Other mediums 111 may include, but are not limited to, petri dishes, vacuums, or similarly functioning devices, any acoustically homogeneous in-viscid medium in a water tank, in petri dishes or in a water-saturated porous sample, etc. However, the medium 111 is not limited to any optically absorbing medium with wavelength-scale thickness, for ballistic region, quasi-ballistic region or diffused region. For example, the medium 111 may include ocean water, biological fluids, blood, tissue, etc. Accordingly, the target object 112 may be illuminated by the OAM light beam 105 having a convenient spatial shape. In one embodiment, the target object 112 may include, but is not limited to, biological molecules and/or tissues, such as soft tissues, mastectomy specimens, single red blood cells, etc.

In a further embodiment, the target object 112 may absorb energy from the OAM light beam 105, such as electromagnetic (EM) radiation, based on the photoacoustic effect that converts optical energy into acoustic energy. The absorbed energy may, in one embodiment, convert to heat, which may cause the temperature of the target object 112 to increase and/or increase the size of the target object 112. This may be referred to as thermal expansion. In photoacoustic tomography, thermal expansion results from a temperature increase, which is caused by the absorption of externally applied radiation of, for example, pulses electromagnetic (EM) waves. The thermal expansion in the target object 112 may generate acoustic pressure and/or acoustic waves in the medium 111, such as mechanical stress, which may result in ultrasonic emissions 115, such as ultrasonic waves. In some embodiments, the pressure increase travels throughout the target object 112 similar to an ultrasonic wave having a frequency content of several tens of megahertz (MHz).

In one embodiment, the OAM modes of a reflected acoustic OAM spectrum 114 are preserved in the resulting ultrasonic emissions 115 (e.g., acoustic waves). Accordingly, a reflected acoustic OAM spectrum 114 associated with the target object 112 may be generated and/or outputted. The OAM spectrum 114 is a parameter that may be used to characterize the OAM light beam 105 after the OAM light beam 105 has been absorbed by the target object 112. For example, when the OAM light beam 105 having a OAM-mode, such as a non-negative mode, impinges on a target object 112, the OAM light beam's 105 angular momentum may be transferred on/in the target object 114 and may be carried by the resulting ultrasonic emissions 115. In some embodiments, due to thermo-acoustic effect, the absorbed energy from the OAM light beam 105 may be converted to heat, causing the target object 112 to slightly expand in volume, which further produces the ultrasonic emissions 115 (e.g., acoustic OAM wave) that propagates outward in all directions at lower frequency. Due to unique characteristics of spiral flow of electromagnetic energy and helical wavefront of the OAM light beam 105, OAM modes may be preserved in the resulting acoustic waves 115. Therefore, the ultrasonic emissions 115 may be used to generate a reflected acoustic OAM spectrum 114 from the target object 112. While the reflected OAM spectrum 114 and the ultrasonic emissions 115 are shown separately in FIG. 1, it should be understood that the ultrasonic emissions 115 generated from the target object 112 may include the reflected OAM spectrum 114. However, for simplification, the reflected OAM spectrum 114 and the ultrasonic emissions 115 are shown separately for illustrative purposes.

In a further embodiment, the generated ultrasonic waves 115 may be detected by, for example, an ultrasonic transducer (not shown), to provide image sensing and/or image reconstruction of the target object 112, which will be described in further detail below. The different optical absorption rates in the target object 112, such as the absorption rates in biological tissues, may be generally related to a variation in the molecules of the target object 112. Accordingly, variations in soft tissues with different optical absorption properties may be clearly identified, as well as temperature, chemical environment, and particle flow monitoring of a biological tissue. For example, the ultrasonic emissions 115 may provide information to generate an image of the target object 112, which offers strong contrast between optically absorbing objects within the target object 112.

In an embodiment, the information related to the target object 112 may be carried by the shape of the acoustic OAM spectrum 114, its bandwidth, or weights of prescribed eigenstates, which may be included in the ultrasonic emissions 115. Accordingly, the corresponding OAM spectrum 114 may be analyzed using a multiple input multiple output (MIMO) device with a digital signal processor (DSP) and/or coherent detection to provide a high resolution image of the target object 112. A digital signal processor (DSP) may be a specialized processor to measure, filter and/or compress continuous analog signals.

Figure 2:
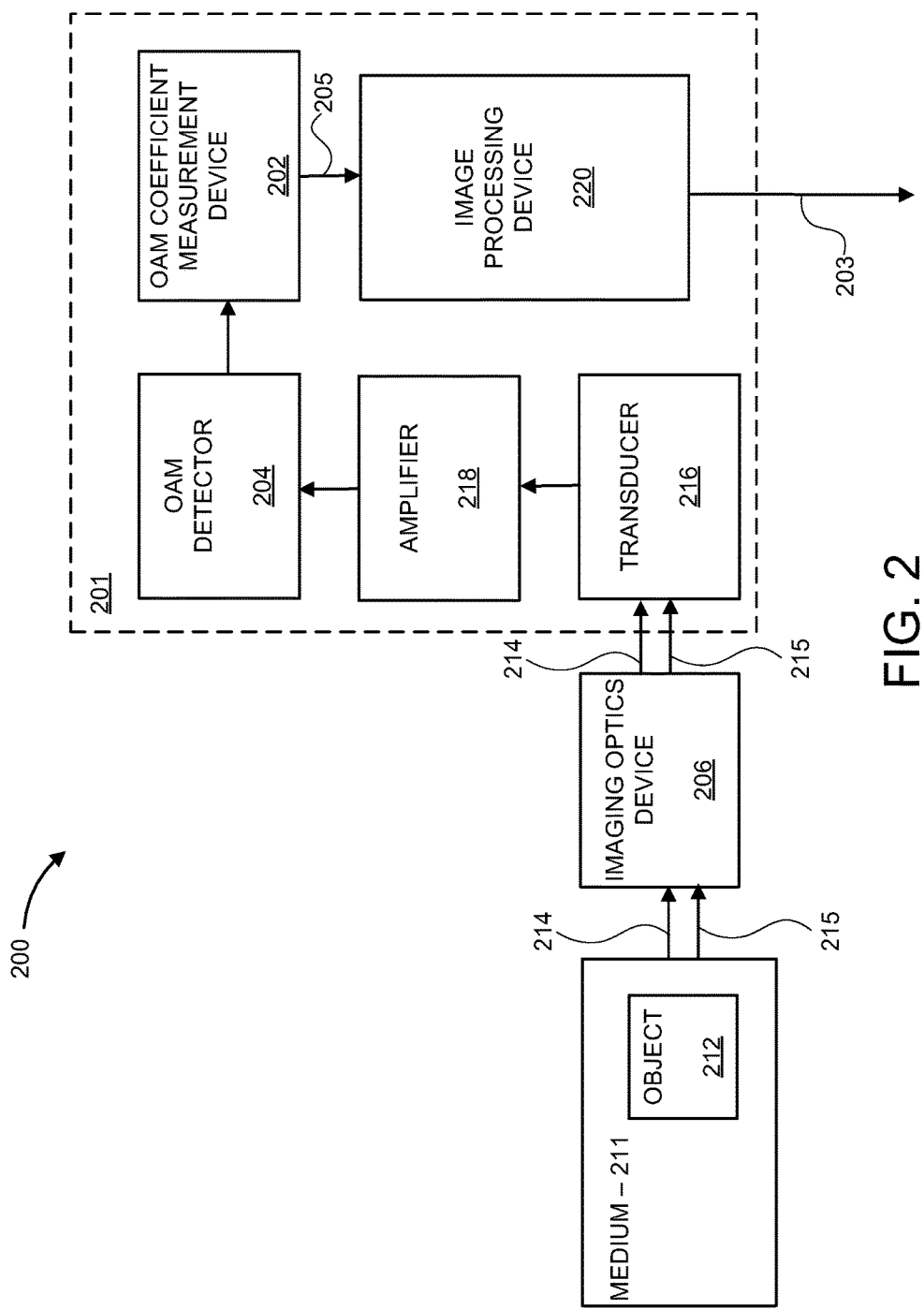
FIG. 2 shows an exemplary system for a receiver-side remote sensing system using photoacoustic tomography with orbital angular momentum (OAM) for object recognition of a target object, in accordance with an embodiment of the present principles.

Now referring to FIG. 2, a receiver-side optical OAM-based photoacoustic tomography system 200 using orbital angular momentum (OAM) for object recognition of a target object is illustratively depicted. It should be noted that medium 211 and/or target object 212 may be the same medium 111 and/or target object 112 depicted in FIG. 1, respectively. In addition, OAM spectrum 214 and/or ultrasonic emission 215 may be the same or similar to the OAM spectrum 114 and/or ultrasonic emission 115 of FIG. 1, respectively. As described above, the reflected OAM spectrum 214 may be included in the ultrasonic emissions 215, however, for illustrative purposes, the reflected OAM spectrum 214 and the ultrasonic emissions 215 are shown separately.

It should further be noted that the optical OAM-based photoacoustic tomography system 200 and/or receiver 201 may be implemented in either transmissive or reflective modes. For example, when the receiver-side optical OAM-based photoacoustic tomography system 200 of FIG. 2 is implemented in the reflective mode, the OAM spectrum 214 corresponding (e.g., reflected from) the target object 212 travels back through the transmitter-side optical OAM-based photoacoustic tomography system 100 in the reverse direction. In such a scenario, the imaging optics device 206 in FIG. 2 may be identical to the imaging optics device 106 of FIG. 1.

In an embodiment, when the receiver-side optical OAM-based photoacoustic tomography system 200 and/or receiver 201 of FIG. 2 is implemented in the reflective mode, the receiver-side components of the receiver 201, namely an OAM detector 204 and/or OAM coefficient measurement device 202 may also be collocated with the transmitter-side components of the transmitter 101 of FIG. 1, namely OAM generator 104. For example, the OAM generator 104 of FIG. 1 may be configured to provide the same or similar functions of the OAM detector 206 and/or OAM coefficient measurement device 202 of FIG. 2. As another example, a transducer, such as traducer 216, may be included in the transmitter 101 when performing in the reflective mode. In addition, further embodiments described herein below relating to the receiver 201 of FIG. 2 may be implemented in the transmitter 101 of FIG. 1. Accordingly, when the receiver-side optical OAM-based photoacoustic tomography system 200 and/or receiver 201 of FIG. 2 is implemented in the reflective mode, the receiver 201 may be the same as the transmitter 101 of FIG. 1. For ease of illustration, the embodiments of the OAM detector 204 and the OAM coefficient measurement device 202 will be described with reference to the receiver 201 implemented in the transmissive mode.

In another embodiment, the receiver-side optical OAM-based photoacoustic tomography system 200 and/or receiver 201 may be implemented in the transmissive mode. In the transmissive mode, the reflected acoustic OAM spectrum 214 and/or ultrasonic emissions 215 generated from the target object 212, which may include acoustic OAM spectrum information, may be transmitted through a second imaging optics device 206. In an embodiment, the second imaging optics device 206 may include one or more lenses, a collimator, a multiplexer (e.g., a demultiplexer), a beam splitter, etc. The second imaging optics device 206 may also include, for example, an amplifier configured to send wavelengths of light (e.g., the OAM spectrum 214) and/or ultrasonic emissions 215 to another device waiting to receive the information, such as the receiver 201. For example, the second imaging optics device 206 may direct the OAM spectrum 214 and/or ultrasonic emissions 215 to the receiver 201 of the receiver-side optical OAM-based photoacoustic tomography system 200.

In an embodiment, the receiver-side optical OAM-based photoacoustic tomography system 200 of FIG. 2 includes a receiver 201 configured to receive and/or measure the reflected OAM spectrum 214 and/or ultrasonic emissions 215. In a further embodiment, the receiver 201 may be configured to exploit the reflected OAM spectrum 114 and/or ultrasonic emissions 215 for remote sensing, including providing high resolution spatial feature recognition and object identification using optical OAM-based photoacoustic tomography. For example, the receiver 201 may be configured to provide a high resolution image of the target object 212.

In one embodiment, the receiver 201 and/or the receiver-side optical OAM-based photoacoustic tomography system 200 may include at least one transducer 216. The transducer 216 may convert ultrasonic waves 215 to electrical signals to provide information corresponding to the target object 212 for image sensing and/or image reconstruction of the target object 212. For example, when the target object 212 absorbs energy from the OAM light beam, converts the energy into heat, and generates acoustic waves and/or ultrasonic emissions 215 in the target object 212 and/or medium 211, the transducer 216 may be configured to detect and/or measure the ultrasonic emissions 215 which may include OAM modes from the acoustic OAM spectrum 214, such as the frequency content of the ultrasonic emissions 215, to provide information to generate a high resolution image 203 of the target object 212. The transducer 216 may include, but is not limited to, an ultrasonic transducer, an array of transducers, or any similarly functioning devices configured to detect ultrasonic emissions 215 and/or convert one form of energy into another.

In some embodiments, a transducer array 216 may be placed around the target object 112 to simultaneously receive the ultrasonic waves 215 emitted at any given time point, which reflects the optical absorption contrast via the OAM spectrum 214 in the target object 212. The transducer 216 may be configured to integrate initial photoacoustic pressures over a spherical surface to map the original optical energy deposition in the tissue of the target object 212, which may then be inverted by, for example, an iteration-based time reversal reconstruction method. The transducer 216 may include a micro-ring resonator for acoustic detection, a thin plate for optoacoustic generation, and/or a dichroic filter to switch between imaging modes. Furthermore, to detect azimuthally dependent OAM modes in the ultrasonic emissions 215 (e.g., acoustic wave) to form an image, OAM fields may be associated with acoustic vortices, which can be realized in devices with cylindrical symmetry and identified by a phase singularity with respect to the symmetry axis. In other words, to map the laser-induced initial pressure rise distribution for different OAM modes, the transducer 216 may include a circular array of radially polarized piezoelectric transducers in which each array element (e.g., of a transducer array) may be energized independently, controlling the phase and amplitude of the acoustic wave applied to each element of the transducer array.

In a further embodiment, the receiver 201 may further include at least one amplifier 218. For example, the amplifier 218 may be an electronic device configured to increase the power of a signal, such as the signal detected at the transducer 216. The amplifier 218 may include, but is not limited to, a pre-amplifier, which may be further configured to provide an electronic signal that has been amplified. A pre-amplifier may have several advantages, including reduction of noise and/or interference signals, amplification of signal strength without degrading signal-to-noise ratio (SNR), etc. In some embodiments, the amplifier 218 may be configured to equalize the modal gain in all OAM modes. Due to the difference in mode distribution, gain equalization may be difficult in OAM multiplexing. To achieve exceptionally well equalized modal gain, the amplifier 218 may provide amplification of signal strength for certain OAM modes.

In an embodiment, the receiver 201 may include at least one OAM detector 204 (e.g., an OAM sorter). The OAM detector 204 may be configured to measure the reflected acoustic OAM spectrum 214 and/or OAM modes of the OAM spectrum 214. In an embodiment, the OAM detector 204 may be configured to measure a set of OAM modes of the reflected acoustic OAM spectrum 214 associated with the target object 212. OAM is one basis of spatial modes to describe light's spatial degree of freedom, which in contrast to other bases of spatial modes, such as the LP-modes of an optical fiber waveguide, is associated with an intrinsic property of light, such as its ability to possess a quantized value of OAM per photon. Aside from being able to obtain high resolution information about an object, OAM can also be transferred to atoms and molecules via absorption and emission selection rules, which may be exploited to gain additional information about the target object 212, according to the present principles. In one embodiment, the OAM detector 204 and/or at least one OAM coefficient measurement device 202 may be configured to measure the reflected acoustic OAM spectrum 214 and/or OAM modes to provide a high resolution image 203 of the target object 212, which will be described in further detail below.

In a further embodiment, the receiver-side optical OAM-based photoacoustic tomography system 200 and/or receiver 201 may also include at least one OAM coefficient measurement device 202. The OAM coefficient measurement device 202 may be configured to determine and/or output coefficient values 205. In one embodiment, the at least one OAM coefficient measurement device 202 may be configured to extract OAM coefficient values 205 from the reflected acoustic OAM spectrum 214 measurement relating to at least one of the amplitude value and relative phase value of each OAM mode and/or amount of power present in each OAM mode. In another embodiment, the coefficient values 205 may include a measurement of the light power of each OAM mode that makes up an object image, a measurement of the light power of one OAM mode of interest, a simultaneous measurement of the light power of multiple OAM modes of interest, a filtering of all OAM modes except the OAM mode of interest such that the coefficient is then the light power of that OAM mode, etc. It should be noted that using the OAM spectrum 214 and/or the coefficient values 205, such as to discriminate between different target objects by measuring the full OAM mode spectrum and/or full set of complex coefficients, may provide full image reconstruction 203 of the target object 212.

In some embodiments, the OAM detector 204 and/or the OAM coefficient measurement device 202 may distinguish objects of distinct shapes via their OAM spectrum information. In some embodiments, the OAM detector 204 and/or OAM coefficient measurement device 202 of FIG. 2 may be identical to the OAM generator 104 of FIG. 1 and may have various implementations. It should be further noted that the receiver 201 of the receiver-side optical OAM-based photoacoustic tomography system 200 may include more than one OAM detector 204, as will be described in further detail below.

In an embodiment, the receiver 201 of the receiver-side optical OAM-based photoacoustic tomography system 200 may further include at least one image processing device 220. For example, the image processing device 220 may be configured to receive, as input, the OAM coefficient measurement values 205 and/or the ultrasonic emission measurements, including the OAM spectrum 214, to generate a high resolution image 203 of the target object 212. The OAM-based photoacoustic tomography system may provide 3-Dimensional (3D) photoacoustic molecular imaging with improved spatial resolution and multiplexing capabilities, combined with high penetration depth and high selectivity based on light, rather than sound or radio frequency. In addition, the present principles may perform at high scanning speeds and maintain sensitivity regardless of scanning depth. Moreover, the present principles provide optical imaging, such as sensitive optical absorption contrast, as well as acoustic imaging, which may be low acoustic scattering in soft tissue. The present principles provides safer illumination sources, such as non-ionizing radiation, and may encode information in infinite-dimensional OAM states, which makes it speckle-free and sensitive to phase gradients and discontinuities when applied to in vivo biological tissues.

Figure 3:
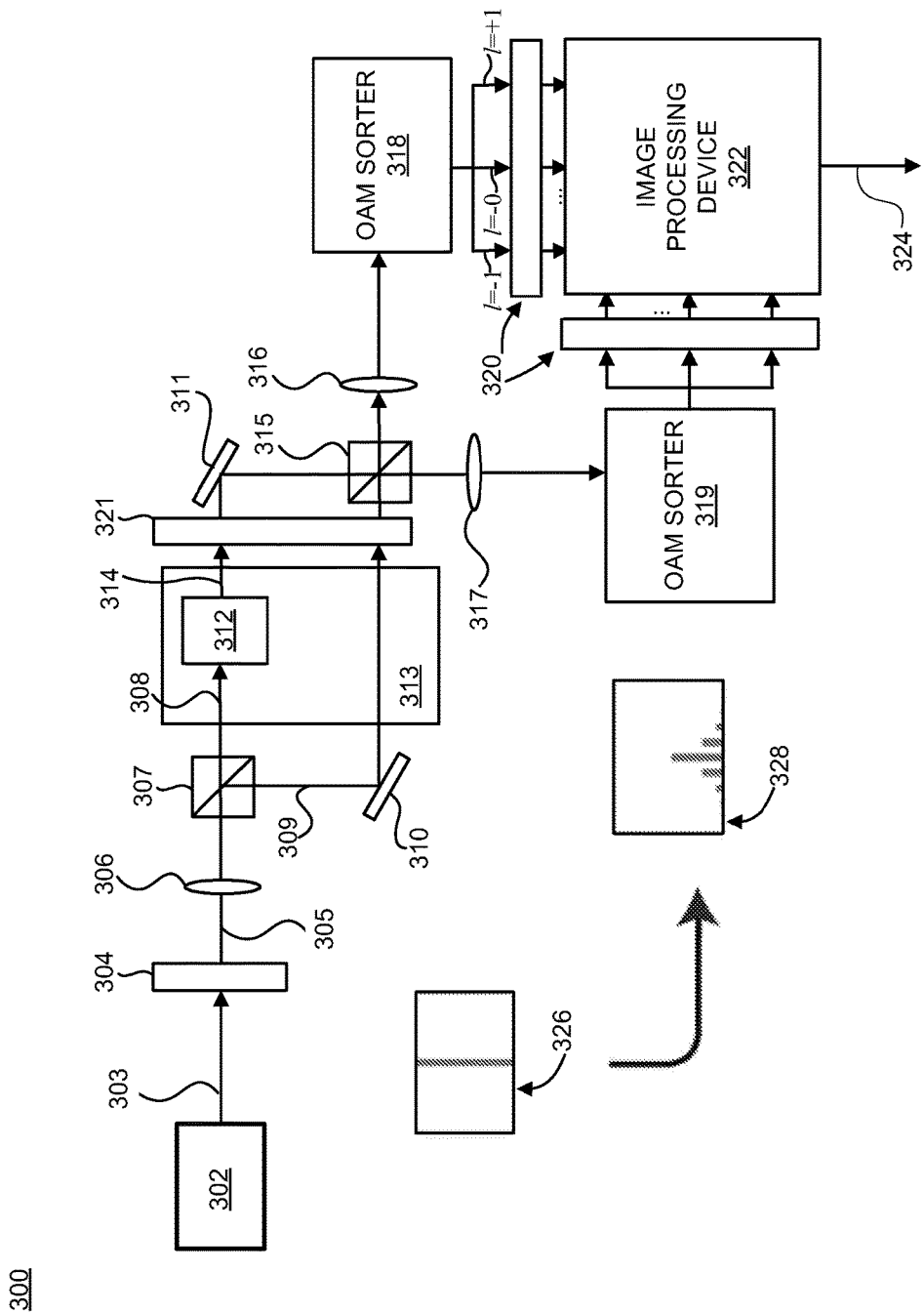
FIG. 3 shows an exemplary system for remote sensing using photoacoustic tomography with orbital angular momentum (OAM) for object recognition of a target object, in accordance with an embodiment of the present principles.

Now referring to FIG. 3, an exemplary system of an optical OAM-based photoacoustic tomography method/system 300 for object recognition using a Mach-Zehnder interferometer is illustratively depicted. A Mach-Zehnder interferometer is a device used to determine, for example, the relative phase shift variations between two collimated light beams derived by splitting light from a single source. For example, the phase shifts between the two beams may be caused by a change in length of one of the paths. In an embodiment, the Mach-Zehnder interferometer of system 300 may be used to, for example, measure pressure, density, temperature changes, and/or measure acoustic waves generated in an object by irradiation with laser beams, etc. In an embodiment, the system 300 may include a light source 302, such as a pump laser, to generate a light beam 303 having an OAM spectrum. For example, the light beam 303 may include an input spiral spectrum 326. An OAM generator 304, such as a beta-barium borate non-linear crystal, may apply at least one OAM mode on the light beam 303 to generate an OAM light beam 305.

As shown in FIG. 3, following the OAM generator 304, the OAM light beam 305 may be applied as input to at least one imaging optics device 306, according to one embodiment, to collimate the light beam. The at least one imaging optics device 306 may include, but is not limited to, a lens, a plurality of lenses arranged in a series, microscope objective(s), or free-space optics, etc. In a further embodiment, the OAM light beam 305 (e.g., a collimated beam) may be applied as input to a first multiplexer 307, such as a beam splitter. The multiplexer 307 may be configured to split the OAM light beam 305 into two or more light beams. For example, the multiplexer 307 may split the collimated beam 305 into at least two resulting beams, namely a sample beam 308 and a reference beam 309, both of which may include at least one OAM state. In one embodiment, the multiplexer 307 may impose a phase shift on the sample beam 308 and/or the reference beam 309.

In an embodiment, the sample beam 308 may be transmitted towards a target object 312 submerged and/or otherwise contained in a medium 313. The target object 312 may absorb the OAM light beam 305 and/or sample beam 308 and thereby generate ultrasonic emissions 314 having a reflected OAM spectrum 328 (e.g., an output spiral spectrum), such as an acoustic OAM spectrum, corresponding to the target object 312. As previously described, the reflected OAM spectrum 328 may be carried by the ultrasonic emissions 314. In a further embodiment, the reference beam 309 may be transmitted through the medium 313 and/or a free-space channel, such as air, water, etc., to provide reference measurements (e.g., phase measurements of the wavelength). In an embodiment, a transducer 321 may be configured to detect the ultrasonic emissions 314, as described above. In a further embodiment, the sample beam 308 and/or ultrasonic emissions 314, and the reference beam 309, may be directed to a second multiplexer 315 by using one or more spatial light modulators 310, 311. The second multiplexer 315 may be the same or different than the first multiplexer 307. In an embodiment, the second multiplexer 315 may alter the outgoing direction with respect to the incoming direction of the sample beam 308 and/or the reference beam 309, and/or may produce the recombination of the two beams (e.g., the sample beam 308 and/or the reference beam 309) with conjugate interference signals for efficient demultiplexing and down-converting.

The spatial light modulators (SLM) 310, 311 may include a device configured to modulate and/or impose spatially varying modulation on the sample beam 309 and/or reference beam 309. Spatially varying modulation is a modulation imposed on a beam of light through a spatial light modulator (SLM) to generate orbital angular momentum (OAM) beams, which relies on the method changing properties of the modulation material. SLMs may provide, but are not limited to, good reconfigurability and reproducibility, fast switching time, accommodating diverse incident polarizations, and high degree of flexibility.

In a further embodiment, the sample beam 308 and/or ultrasonic emissions 314, and the reference beam 309, may be directed towards one or more imaging optics devices 316, 317 and/or OAM sorters 318, 319. Imaging optics devices 316, 317 may be the same as or similar to imagining optics devices 310, 311. In an embodiment, the intensities of the resulting beams, namely the sample beam 308 and the reference beam 309, may be different, allowing the OAM sorters 318, 319 to determine the phase shift caused by the target object 312. The OAM sorters 318, 319 may provide the same and/or similar functions as the OAM detector 204 and/or OAM coefficient measurement device 202 of FIG. 2. For example, the OAM sorters 318, 319 may be configured to distinguish between multiple orthogonally decoded OAM modes to provide high spatial resolution information. As illustrated in FIG. 3, a first and second OAM sorter 318, 319 may be configured to detect and determine the output of the OAM spiral spectrum of the sample beam 308 and the reference beam 309. For example, the intensities of the light beam of the sample beam 308 and the reference beam 309 may be different due to the presence of the target object 312, thereby allowing the OAM sorters 318, 319 to determine the phase shift caused by the target object 312. Accordingly, the transducer 321 may detect the ultrasonic emissions 314 having the reflected OAM spectrum 328 and the OAM sorter 319 may be configured to detect the OAM spectrums and/or OAM modes of the sample beam 308 to distinguish imaging properties of the target object 312, which may be compared to the OAM spectrum of the reference beam 309 for comparison. Accordingly, the OAM sorter 318 may be configured to determine the OAM modes of the OAM spectrum of the reference beam 309.

In an embodiment, one or more band-pass filters 320 may be used to accept frequencies within a predetermined range and/or rejects frequencies outside the predetermined range. In some embodiments, as shown in FIG. 3, the bandpass filters 320 may accept and/or reject different OAM modes, such as l=−1, l=0, and/or l=1. Additional OAM modes may be accepted and/or rejected by the bandpass filters 320. The sample beam 308 and/or ultrasonic emissions 314 having the reflected OAM spectrum 328 properties associated with the target object 312, and the reference beam 309, may be employed to determine the phase shift caused by the target object 312. In a further embodiment, an image processing device 322 may generate a high resolution image 324 based on the ultrasonic emissions 314 and/or reflected OAM spectrum 328. For example, the image processing device 322 may include a balanced photodetector.

Accordingly, the optical OAM-based photoacoustic tomography method/system 300 may detect acoustic pressure by scanning the transducer 321, which may include a transducer array, over a surface that encloses the photoacoustic source, such as the target object 312. The internal source distribution of the image of the target object 312 may be reconstructed using a universal back-projection algorithm implemented in the image processing device 322 to provide a high resolution image 324. Main advantages of OAM processing occurs due to the additional degree of freedom of the OAM light beam 305 to increase the overall number of parallel channels (e.g., OAM modes) with each independent channel on an orthogonal spatial mode, which makes it appropriate for broadband absorption detection of frequency-domain photoacoustic tomographic reconstructions. Accordingly, the speed for image acquisition/reconstruction may increase significantly due to more orthogonal channels, while the overall cost of the sensing system may be reduced due to fewer transducers needed.

Figure 4:
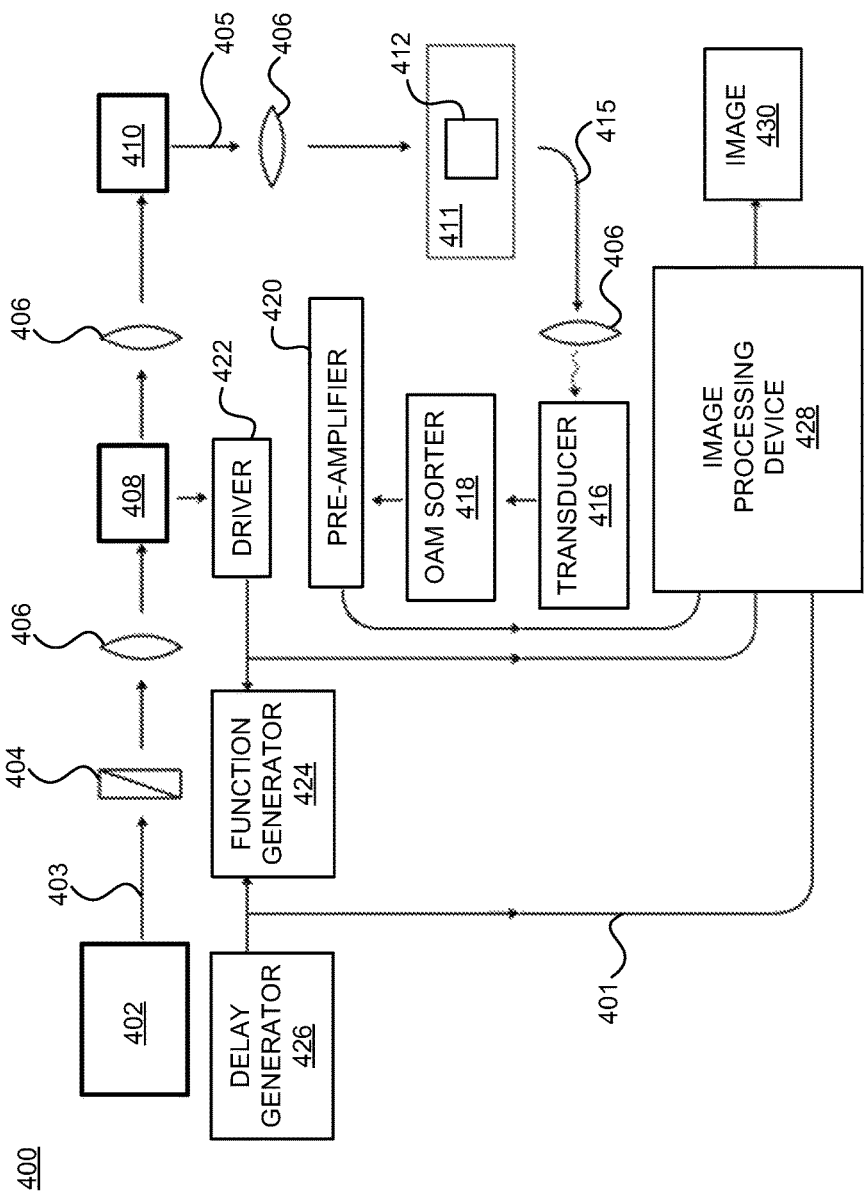
FIG. 4 shows an exemplary system for remote sensing using photoacoustic tomography with orbital angular momentum (OAM) for object recognition of a target object, in accordance with an embodiment of the present principles.

Now referring to FIG. 4, an exemplary system of an optical OAM-based photoacoustic tomography method/system 400 for object recognition is illustratively depicted. In FIG. 4, the optical OAM-based photoacoustic tomography system 400 may include a light source device 402, a multiplexer 404, an array of imaging optics devices 406, an acousto-optic modulator (AOM) 408, a OAM generator 410, an ultrasonic transducer 416, an OAM sorter 418, a pre-amplifier 420, a driver 422, a function generator 424, a delay generator 426, and an image processing device 428. The light source device 402 may include a frequency-swept laser source to generate a light beam 403. The acousto-optic modulator (AOM) 408 may be configured to control the power, frequency and/or spatial direction of the laser beam 403. In some embodiments, the AOM 408 may diffract and/or shift the frequency of the light beam 403 using sound waves (e.g., radio-frequency waves) to provide a light beam 403 with a controlled frequency. In addition, the phase of the light beam 403 may also be shifted by the phase of the sound wave generated by the acousto-optic modulator (AOM) 408. In a further embodiment, the AOM 408 may be configured to generate pulses to the driver 422 and/or function generator 424 to provide a synchronization signal 401, as will be described in further detail below.

The OAM generator 410 may be configured to receive the light beam 403 and impose OAM modes on the light beam 403 to generate an OAM light beam 405. The OAM light beam 405 may be transmitted through a spatial light modulator 410 and directed towards the target object 412, wherein the target object 412 may be surrounded by a medium 411.

In an embodiment, ultrasonic emissions 415 formed by thermal expansion in the target object 412 may be generated/emitted and received by the ultrasonic transducer 418. The ultrasonic emissions 415 may include the reflected acoustic OAM spectrum properties corresponding to the target object 412, which may be employed to generate a high resolution image 430 of the target object 412. The ultrasonic transducer 416 may be configured to detect the ultrasonic emissions 415 and the OAM sorter 418 may be configured to detect the reflected OAM spectrum and/or corresponding OAM modes. In a further embodiment, the pre-amplifier 420 may be configured to equalize modal gain by amplifying signal strength for certain OAM modes prior to image processing.

The measurements from the reflected OAM spectrum carried by the ultrasonic emissions 415 may be received by the image processing device 428 to generate a high resolution image 430 corresponding to the target object 412. The image processing device 428 may include, for example, a local oscillator, A/D Converters, a digital signal processing unit, and/or computer. For example, a local oscillator (LO) may be configured to provide a stable frequency with low harmonics, effectively driving subsequent stages of circuitry, and thus improving the performance of the image processing device 428. An analog-to-digital converter (ADC) may be configured to convert voltage to a digital number that represents the quantity's amplitude. A digital signal processing unit (DSP) and/or computer may be employed to run a universal back-projection algorithm for photoacoustic tomographic reconstructions to provide a high resolution image 430 of the target object 412.

In a further embodiment, a function generator 424 may be employed to provide a synchronization signal 401. The synchronization signal 401 may provide an original frequency of the light beam 403 to the image processing device 428 for comparison purposes. For example, the image processing device 428 may compare the OAM measurements and the synchronization signal 401 to generate a high resolution image 430. In some embodiments, a driver 422 may be configured to receive the input of the light beam 403 (e.g., frequency of the light beam 403) and may provide pulses to the function generator 424 to generate the synchronization signal 401. In further embodiments, a delay generator 426 may be configured to provide logic transitions and/or provide pulse delay to the function generator 424 to provide a delayed synchronization signal. Accordingly, the function generator 424 may provide electrical waveforms by a synchronization signal 401 to the image processing device 428 to improve the signal processing performance.

Figure 5:
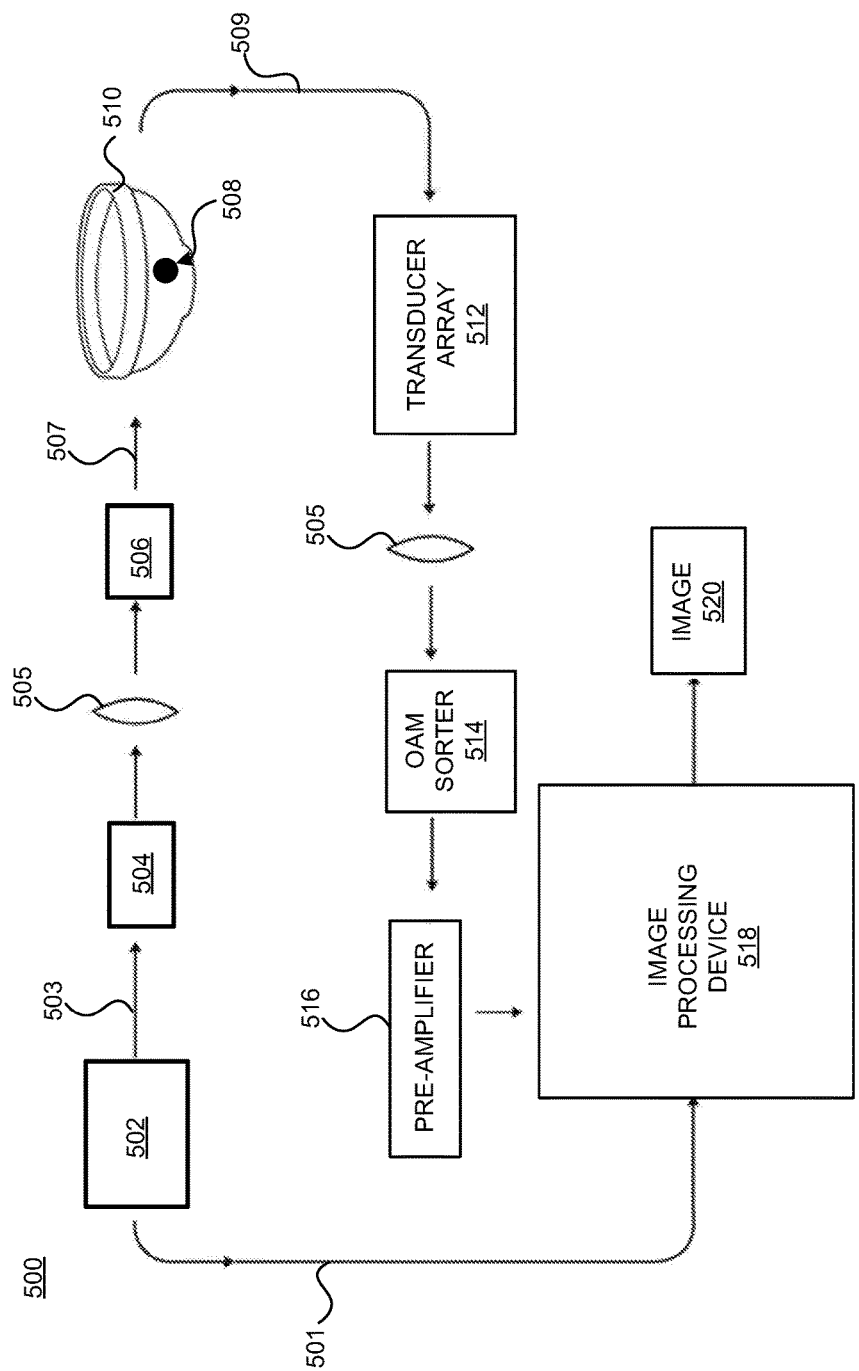
FIG. 5 shows an exemplary system for remote sensing using photoacoustic tomography with orbital angular momentum (OAM) for object recognition of a target object, in accordance with an embodiment of the present principles.

Now referring to FIG. 5, an exemplary system of an optical OAM-based photoacoustic tomography method/system 500 for object recognition is illustratively depicted. For example, the optical OAM-based photoacoustic tomography system 500 may include opto-acoustic imaging for breast cancer detection. In FIG. 5, the optical OAM-based photoacoustic tomography system 500 may include a light source device 502, an amplifier 504, an array of imaging optics devices 505, an OAM generator 506, an array of transducers 512, an OAM sorter 514, a pre-amplifier 516, and an image processing device 518.

The light source device 502 may include a pulsed laser source to generate a light beam 503. The amplifier 504 may be configured to amplify an optical signal, such as light beam 503. For example, the amplifier 504 may include an optical amplifier, such as an erbium doped fiber amplifier (EDFA), configured to amplify the light beam 503 without converting the light beam 503 to an electrical signal first. The OAM generator 506 may include, for example, a spatial light modulator, configured to apply at least one OAM mode on the light beam 503 to generate an OAM light beam 507. The OAM light beam 507 may be directed toward a target object 508, such as a breast tissue, placed in a medium 510, such as a breast tester. As described above, the energy from the OAM light beam 507 may be absorbed by the target object 508 and may generate ultrasonic emissions 509, which may include a reflected acoustic OAM spectrum, such that the ultrasonic emissions 509 may be detected by the array of transducers 512.

During OAM demultiplexing when the ultrasonic emissions 509 are received in the OAM sorter 514, the twisting phase fronts of OAM modes are converted into the L-dependent spatial positions via a log polar optical element transformation at its output, whereas the single mode optical fiber array is located at the OAM sorter 514 output to collect acoustic waves from each L-dependent spot for coherent detection, and therefore operates as a demultiplexer. In an embodiment, the optical OAM-based photoacoustic tomography system 500 may be used for breast cancer detection by utilizing pulsed optical illumination and ultrawide-band ultrasonic detection of resulting opto-acoustic signals.

In an embodiment, the acoustic OAM spectrum included in the ultrasonic emissions 509 corresponding to the target object 508 is generated and directed to the OAM sorter 514 for further processing. In a further embodiment, at least one of the measurements from the OAM spectrum and/or the ultrasonic emissions 509 are pre-amplified by the pre-amplifier 516 and/or received by the image processing device 518 to generate a high resolution image 520 corresponding to the target object 508. The image processing device 518 may include, for example, an A/D Converter and/or microprocessor. The analog-to-digital converter (ADC) and/or microprocessor may include, for example, converting means to convert voltage to a digital number that represents the quantity's amplitude.

In a further embodiment, a laser pulse synchronization signal 501 is generated at the light source 502, and may be transmitted to the image processing device 518. In an embodiment, the image processing device 518 may be configured to compare the energy output of the laser pulse synchronization signal 501 and the energy output measured by the transducer 512. For example, the laser output energy may be measured at each wavelength and/or compared, such as the laser intensity fluctuations, to further identify features of the target object 508 and/or generate a high resolution image 520. In some embodiments, the image processing device 518 may employ the synchronization signal 501 for accurate synchronization and/or correct operation. For instance, if switches do not operate with the same clock rates, slips may occur and degrade the imaging performance. Thus, a drive signal generating circuit may be configured to generate an imaging synchronization signal 501 and provide the imaging synchronization signal 501 to the image processing device 518 to increase performance in generating the image 520.

Figure 6:
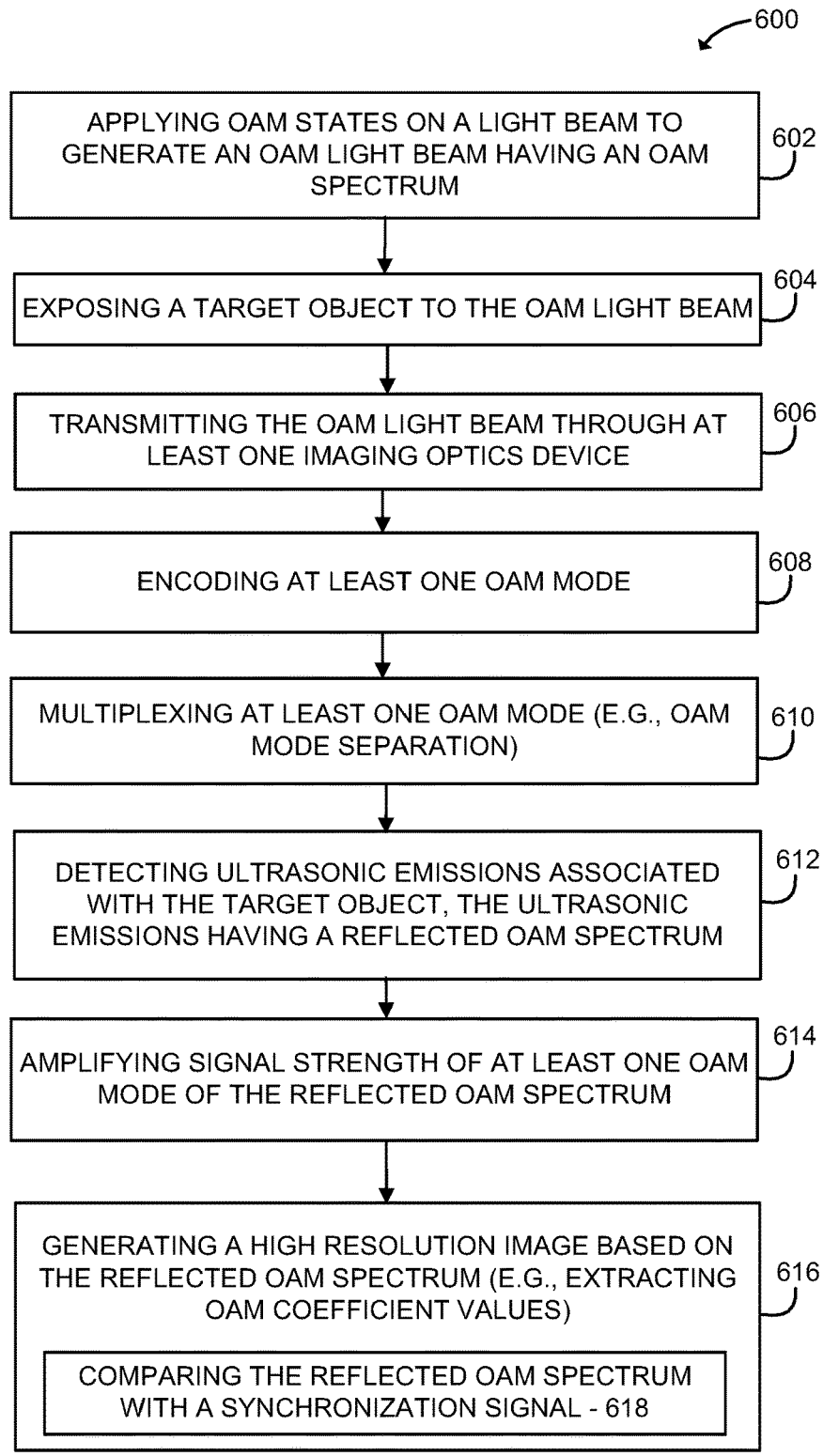
FIG. 6 is a block diagram illustratively depicting an exemplary method using photoacoustic tomography with orbital angular momentum (OAM) for object recognition of a target object, in accordance with an embodiment of the present principles.

Now referring to FIG. 6, a method 600 for remote sensing using orbital angular momentum (OAM)-based photoacoustic tomography for object recognition is illustratively depicted according to one embodiment of the present principles. Advantageously, the method 600 may employ orbital angular momentum (OAM) on a light beam to obtain high resolution feature identification in LIDAR-based remote sensing and to provide effective compressive imaging more efficient than pixel-by-pixel imaging techniques, with the added advantage of having low cost and less complexity. The method 600 can be performed, for example, by any of system 100 of FIG. 1, system 200 of FIG. 2, system 300 of FIG. 3, system 400 of FIG. 4, and/or system 500 of FIG. 5.

In block 602, arbitrary OAM states/modes may be applied on a light beam before characterizing the target object to generate an OAM light beam. In accordance with the present principles, the arbitrary OAM states may include non-zero OAM states. The light beam may include a laser beam and may intrinsically have angular momentum. In one embodiment, the OAM light beam may be transmitted by, for example, a light source device according to various embodiments, and may be directed towards the target object, as shown in block 604.

The OAM light beam may be optionally transmitted through at least one imaging optics device, as illustrated in block 606. For example, the imaging optics device may include a lens, a plurality of lenses arranged in a series, etc.

In block 608, the OAM light beam and/or at least one OAM mode may be optionally encoder by, for example, an encoder. For example, the encoder may encode one or more of the OAM modes through the electro-optic tuning of the mode order of ring cavity at different positions in the wavelength domain.

In block 610, the OAM light beam and/or at least one OAM mode may be optionally multiplexed by, for example, a multiplexer. For example, the multiplexer may be configured to provide OAM mode separation and/or conversion at different positions in the wavelength domain.

The OAM light beam may be exposed on the target object, which may be surrounded by a medium. Due to the photoacoustic effect of light, the energy of the light beam may be absorbed by the target object. The OAM light beam may propagate through the target object, providing thermal expansion, and generate ultrasonic emissions, such as ultrasonic waves which may include a reflected acoustic OAM spectrum having corresponding OAM modes, associated with the target object and/or medium.

In block 612, the ultrasonic emissions and/or reflected acoustic OAM spectrum may be received and/or detected by a transducer, such as an ultrasonic transducer, and/or OAM detector, and may be converted into signals and/or spiral eigenstates of OAM (e.g. OAM modes). For example, the eigenstates of OAM may be carried by the shape of the reflected acoustic OAM spectrum. To map the laser-induced initial pressure rise distribution for different OAM modes, a transducer may integrate initial photoacoustic pressures over a spherical surface of a target object, which may be inverted by an iteration-based time reversal reconstruction method. Accordingly, the reflected acoustic OAM spectrum may be associated with the target object and may provide high resolution imaging information of the target object.

In a further embodiment, the signals from the ultrasonic emissions and/or reflected OAM spectrum may be amplified by, for example, an amplifier, as shown in block 614. For example, an amplifier may amplify signal strength for certain OAM modes.

The reflected acoustic OAM spectrum may be measured to generate a high resolution image of the target object, as illustrated in block 616. For example, OAM coefficient values for each OAM mode may be extracted from the reflected OAM spectrum to provide high resolution spatial information associated with the target object. The reflected OAM spectrum may provide optical absorption distribution information (e.g., optical contrast) of the target object. In block 616, an image may be generated with high resolution structural properties of the remote object based on the extracted OAM coefficient values and/or the reflected acoustic OAM spectrum.

In an optional embodiment, a synchronization signal may be generated from the light beam and may be used to compare the frequency shifts between the light beam and the reflected OAM spectrum to generate a high resolution image, as shown in block 618. In addition, it is contemplated that the synchronization signal may include a delay signal, such that a delayed synchronization signal is compared with the reflected OAM spectrum to generate a high resolution image.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

A data processing system suitable for storing and/or executing program code may include at least one processor, e.g., a hardware processor, coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

It should be noted that while the above configuration is illustratively depicted, it is contemplated that other sorts of configurations may also be employed according to the present principles. These and other variations between configurations are readily determined by one of ordinary skill in the art given the teachings of the present principles provided herein, while maintaining the present principles. Moreover, in one embodiment, at least one of the elements described above is processor-based. Further, while one or more elements may be shown as separate elements, in other embodiments, these elements can be combined as one element. The converse is also applicable, where while one or more elements may be part of another element, in other embodiments, the one or more elements may be implemented as standalone elements. These and other variations of the elements are readily determined by one of ordinary skill in the art, given the teachings of the present principles provided herein.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that those skilled in the art may implement various modifications without departing from the scope and spirit of the invention. Those skilled in the art could implement various other feature combinations without departing from the scope and spirit of the invention.

What is claimed is:
1. A method for remote sensing, comprising:
applying at least one orbital angular momentum (OAM) mode on a light beam to generate an OAM light beam having an optical OAM spectrum, the OAM light beam forming a complete infinite-dimensional basis for solutions of a paraxial wave equation in terms of Laguerre-Gaussian (LG) modes, wherein a normalized LG mode at a beam waist is expressed in cylindrical coordinates as:

$$LG_{m,p}(\rho, \varphi) = \left(\frac{2p!}{\pi(|m|+p)!}\right)^{1/2} \frac{1}{\eta}\left(\frac{\sqrt{2}\rho}{\eta}\right)^{|m|} L_p^{|m|}\left(\frac{2\rho^2}{\eta^2}\right)\exp\left(-\frac{\rho^2}{\eta^2}\right)\exp(im\varphi),$$

wherein m represents an on-axis phase singularity of strength, p represents an index, $\rho$ is a radial cylindrical coordinate, $\varphi$ is an azimuthal angle, $\eta$ is the beam waist, and $L_p^{|m|}$ is an associated Laguerre polynomial;

exposing a target object to the OAM light beam such that the target object absorbs energy of the OAM light beam to generate ultrasonic emissions, the ultrasonic emissions having a reflected OAM spectrum associated with the target object; and generating a high resolution image of the target object based on the reflected OAM spectrum.

2. The method according to claim 1, wherein the at least one OAM mode is an arbitrary non-zero OAM state relating to at least one of an amplitude value or a relative phase value of each OAM mode.

3. The method according to claim 1, further comprising extracting OAM coefficient values from the reflected OAM spectrum to generate the high resolution image of the target object.

4. The method according to claim 1, further comprising transmitting the OAM light beam through at least one imaging optics device prior to transmitting the OAM light beam on the target object.

5. The method according to claim 1, wherein generating the high resolution image of the target object includes an iteration-based time reversal reconstruction method.

6. The method according to claim 1, further comprising encoding the at least one OAM mode at different positions in a wavelength domain.

7. The method according to claim 1, further comprising multiplexing the OAM light beam to generate OAM mode separation at different positions in a wavelength domain.

8. The method according to claim 1, further comprising amplifying signal strength of at least one OAM coefficient value of the reflected OAM spectrum.

9. The method according to claim 1, further comprising comparing a frequency of the reflected OAM spectrum with a frequency of a synchronization signal to generate the high resolution image.

10. A receiver for remote sensing, the receiver comprising:
at least one transducer configured to:
receive a generated OAM light beam having an optical OAM spectrum, the OAM light beam forming a complete infinite-dimensional basis for solutions of a paraxial wave equation in terms of Laguerre-Gaussian (LG) modes, wherein a normalized LG mode at a beam waist is expressed in cylindrical coordinates as:

$$LG_{m,p}(\rho, \varphi) = \left(\frac{2p!}{\pi(|m|+p)!}\right)^{1/2} \frac{1}{\eta}\left(\frac{\sqrt{2}\rho}{\eta}\right)^{|m|} L_p^{|m|}\left(\frac{2\rho^2}{\eta^2}\right)\exp\left(-\frac{\rho^2}{\eta^2}\right)\exp(im\varphi),$$

wherein m represents an on-axis phase singularity of strength, p represents an index, $\rho$ is a radial cylindrical coordinate, $\varphi$ is an azimuthal angle, $\eta$ is the beam waist, and $L_p^{|m|}$ is an associated Laguerre polynomial; and detect ultrasonic emissions generated by a target object, wherein the ultrasonic emissions include a reflected orbital angular momentum (OAM) spectrum associated with the target object;

at least one OAM detector configured to detect the reflected OAM spectrum; and an image processing device having a processor to generate a high resolution image of the target object based on the reflected OAM spectrum.

11. The receiver according to claim 10, wherein the at least one transducer includes an array of radially polarized piezoelectric transducers.

12. The receiver according to claim 10, wherein the at least one OAM detector includes at least one of a spatial light modulator, a liquid crystal on silicon spatial light modulator (LCOS-SLM), Q-phase plates, an OAM sorter or a combination thereof.

13. The receiver according to claim 10, wherein the at least one OAM detector is configured to extract OAM coefficient values from the reflected OAM spectrum to generate the high resolution image of the target object.

14. The receiver according to claim 10, further comprising at least one imaging optics device, the at least one imaging optics devices including at least one of a lens, a plurality of lenses arranged in a series, a microscope objective, free-space optics, or a combination thereof.

15. The receiver according to claim 10, wherein the image processing device generates the high resolution image of the target object using an iteration-based time reversal reconstruction method.

16. The receiver according to claim 10, further comprising at least one amplifier configured to amplify signal strength of at least one OAM coefficient value of the reflected OAM spectrum.

17. The receiver according to claim 10, further comprising a drive signal generating circuit configured to generate an imaging synchronization signal, wherein the image processing device is further configured to compare a frequency of the reflected OAM spectrum with a frequency of the synchronization signal to generate the high resolution image.

18. A system for remote sensing, comprising:
a drive signal generating circuit to generate an imaging synchronization signal of a light beam;
a receiver configured to receive a generated OAM light beam having an optical OAM spectrum, the OAM light beam forming a complete infinite-dimensional basis for solutions of a paraxial wave equation in terms of Laguerre-Gaussian (LG) modes, wherein a normalized LG mode at a beam waist is expressed in cylindrical coordinates as:

$$LG_{m,p}(\rho, \varphi) = \left(\frac{2p!}{\pi(|m|+p)!}\right)^{1/2} \frac{1}{\eta}\left(\frac{\sqrt{2}\rho}{\eta}\right)^{|m|} L_p^{|m|}\left(\frac{2\rho^2}{\eta^2}\right)\exp\left(-\frac{\rho^2}{\eta^2}\right)\exp(im\varphi),$$

wherein m represents an on-axis phase singularity of strength, p represents an index, $\rho$ is a radial cylindrical coordinate, $\varphi$ is an azimuthal angle, $\eta$ is the beam waist, and $L_p^{|m|}$ is an associated Laguerre polynomial;

at least one orbital angular momentum (OAM) detector to detect a reflected OAM spectrum, wherein the reflected OAM spectrum is provided by ultrasonic emissions generated from a target object absorbing energy of an OAM light beam; and an imaging processing device having a processor configured to compare a frequency of the synchronization signal with a frequency of the reflected OAM spectrum to generate a high resolution image of a target object.

19. The system according to claim 18, wherein the image processing device generates the high resolution image of the target object using an iteration-based time reversal reconstruction method.

20. The system according to claim 18, further comprising a delay generator configured to generate a delay signal, wherein:
    the drive signal generating circuit generates a delayed imaging synchronization signal of the light beam based on the delay signal; and
    the imaging processing device is further configured to compare a frequency of the delay synchronization signal with the frequency of the reflected OAM spectrum to generate the high resolution image of a target object.

* * * * *